(12) United States Patent
Norland et al.

(10) Patent No.: US 11,957,096 B2
(45) Date of Patent: Apr. 16, 2024

(54) AUTONOMOUS AIRCRAFT SYSTEM FOR POLLINATING PLANTS

(71) Applicant: Arizona Board of Regents on Behalf of the University of Arizona, Tucson, AZ (US)

(72) Inventors: Kyle Tabor Norland, Tucson, AZ (US); Mitzy Oros, Tucson, AZ (US); Evan Westman, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 128 days.

(21) Appl. No.: 17/243,484

(22) Filed: Apr. 28, 2021

(65) Prior Publication Data

US 2021/0329865 A1    Oct. 28, 2021

Related U.S. Application Data

(60) Provisional application No. 63/016,782, filed on Apr. 28, 2020.

(51) Int. Cl.
| | |
|---|---|
| *A01H 1/02* | (2006.01) |
| *B64C 39/02* | (2023.01) |
| *B64D 1/00* | (2006.01) |
| *G05D 1/00* | (2006.01) |
| *G06V 10/44* | (2022.01) |
| *G06V 20/10* | (2022.01) |
| *B64U 10/13* | (2023.01) |
| *B64U 101/00* | (2023.01) |
| *H04N 7/18* | (2006.01) |

(52) U.S. Cl.
CPC ........... *A01H 1/027* (2021.01); *B64C 39/024* (2013.01); *B64D 1/00* (2013.01); *G05D 1/0204* (2013.01); *G05D 1/106* (2019.05); *G06V 10/443* (2022.01); *G06V 20/188* (2022.01); *B64U 10/13* (2023.01); *B64U 2101/00* (2023.01); *H04N 7/18* (2013.01)

(58) Field of Classification Search
CPC ........ A01H 1/027; B64D 1/16; G06V 20/188; B64U 10/13; B64U 2101/00
See application file for complete search history.

(56) References Cited

U.S. PATENT DOCUMENTS

| | | | | |
|---|---|---|---|---|
| 6,212,824 | B1 * | 4/2001 | Orr | A01G 7/00 47/1.01 R |
| 8,553,929 | B2 * | 10/2013 | Motoyama | H04N 1/32288 382/284 |
| 8,781,174 | B2 * | 7/2014 | Tseng | G06F 18/00 382/110 |
| 9,532,508 | B1 * | 1/2017 | Stubbs | H04N 7/183 |
| 2014/0246545 | A1 * | 9/2014 | Markov | B64D 1/16 244/190 |
| 2016/0260207 | A1 * | 9/2016 | Fryshman | A01H 1/027 |
| 2016/0353661 | A1 * | 12/2016 | Caldeira | A01H 1/02 |

(Continued)

*Primary Examiner* — Michael H Wang
(74) *Attorney, Agent, or Firm* — Carin R. Miller, Esq.; Johnson, Marcou, Isaacs & Nix, LLC

(57) ABSTRACT

The systems and methods described herein relate to fully or partially autonomous or remotely operated aerial pollination vehicles that use computer vision and artificial intelligence to automatically detect plants, orient the vehicle to a pollen dispensing position above each plant, and pollinate the individual plants.

19 Claims, 14 Drawing Sheets

(56) References Cited

U.S. PATENT DOCUMENTS

| | | | |
|---|---|---|---|
| 2017/0231213 A1* | 8/2017 | Gordon | A01M 7/0089 |
| | | | 43/132.1 |
| 2018/0065749 A1* | 3/2018 | Cantrell | B64D 1/22 |
| 2019/0183077 A1* | 6/2019 | Ajamian | G05D 1/102 |
| 2020/0022312 A1* | 1/2020 | Gauvreau, Jr. | B64C 39/024 |
| 2020/0120886 A1* | 4/2020 | Geltner | B25J 9/1697 |
| 2021/0379617 A1* | 12/2021 | Chapple | B64C 39/024 |
| 2022/0000051 A1* | 1/2022 | Geltner | G06V 10/10 |
| 2022/0023904 A1* | 1/2022 | Chapple | B05B 12/12 |
| 2022/0039343 A1* | 2/2022 | Miyako | B64C 39/02 |

* cited by examiner

340

Method for an AFV to take station above a plant and relative to a center of the plant

710

Receive coordinates for the center of the plant

720 Account for wind?

No → 730 Set the center of the plant as the dispensing location

Yes → 740 Determine effect of wind speed and direction on dispersed pollen based on height of the AFV above the plant 750 Determine location offset from center to disperse pollen to the plant based on effect of wind speed and direction 760 Set the offset location as the dispensing location 770 Maneuver the AFV to the dispensing location 350, Fig. 3

Figure 7

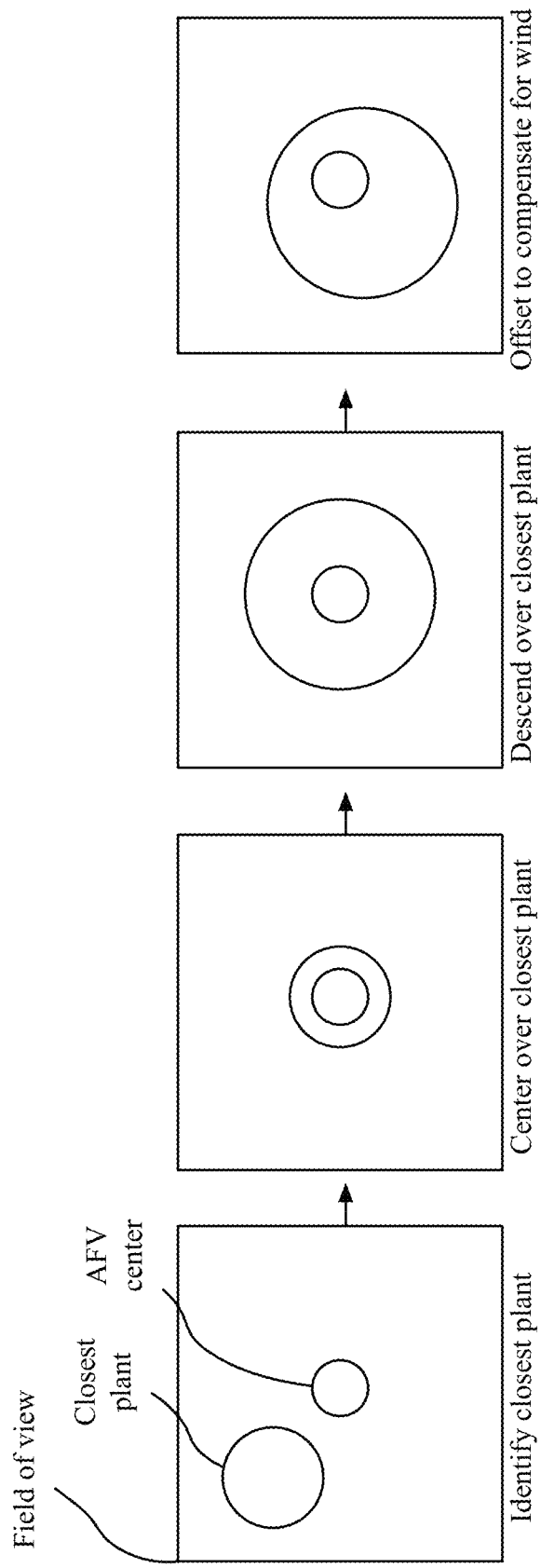

AUTONOMOUS AIRCRAFT SYSTEM FOR POLLINATING PLANTS

CROSS REFERENCE TO RELATED APPLICATIONS

This application claims priority to U.S. Provisional Patent Application No. 63/016,782 filed Apr. 28, 2020 and titled "Automated Drone Pollination System." The entire contents of the above-identified priority application are hereby fully incorporated herein by reference.

TECHNICAL FIELD

The subject matter of this disclosure relates to pollination systems and, more particularly, to automated pollination systems using autonomous aircraft and systems to pollinate plants.

BACKGROUND

A typical plantation may comprise primarily female trees or other plants. This increased ratio of female to male plants maximizes the amount of fruit produced. However, this configuration creates a need for manual pollination to adequately pollinate the female plants.

One conventional pollination process is hand-pollination of individual flowers. This process is time-consuming and may not be practical or possible for large plants, such as trees.

Another conventional pollination process involves operating a mobile blower that sprays pollen onto the flowers. For trees or other large plants, the blower is operated at the base of the tree to blow pollen toward the flowers above the operator. This process, although more cost effective than individual flower pollination by hand, is still costly, labor intensive, inefficient, and inaccurate.

Another conventional pollination process involves pollination from a drone flying above the plants. The drone continuously dispenses pollen contained in a hosiery as it flies over the plants. This process improves upon the mobile blower technique that propels pollen from ground level. However, this conventional drone pollination process requires continuous operation by a drone pilot, as it is not autonomous and also requires continuous dispensing of the pollen to avoid missing plants. This process is also both inaccurate and inefficient, as it pollinates large areas to hit flowers within a small portion of that area, thereby wasting pollen and drone resources, such as available battery charge.

SUMMARY

In certain example aspects described herein, systems and autonomous aircraft for pollinating plants are provided. In an example embodiment, an autonomous aircraft system comprises an image capture device, a pollen dispensing system, a flight control system, and a processor. The flight control system maneuvers the autonomous aircraft higher than a plant and in the general vicinity of the plant. The image capture device captures an image below the autonomous aircraft, and the image includes a top view of the plant. The processor processes the image to differentiate between the plant and ground below the plant, and to determine a center of the plant based on the processed image. The flight control system maneuvers the autonomous aircraft above the plant and relative to the center of the plant. The pollen dispensing system dispenses pollen to the plant.

In certain other example aspects described herein, a computer-implemented method and a computer program product for pollinating plants are provided.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 7 is a block flow diagram depicting a method for an autonomous aircraft to take station above a plant and relative to the center of the plant.

FIGS. 10A, 10B, 10C, and 10D illustrate execution of instructions to position an autonomous aircraft in a dispensing location above a plant.

DETAILED DESCRIPTION OF EXAMPLE EMBODIMENTS

The systems and methods described herein relate to fully or partially autonomous or remotely operated pollination vehicles that use computer vision and artificial intelligence to automatically detect plants, orient the vehicle to a pollen dispensing position above each plant, and pollinate the individual plants.

The technology described herein provides an automated pollination system comprising one or more aircraft that pollinate plants. The system includes a guidance system to facilitate pollination. The guidance system executes a plant identification and centering process that identifies a particular plant and positions the drone above the identified plant. The system also includes a pollen dispenser device coupled to the vehicle to dispense pollen and a graphical user interface that supports the vehicle operation.

More particularly, the system uses computer vision and artificial intelligence to observe, model, and act on its environment to efficiently and safely complete the pollination process. This process includes identification of plants, commands to release pollen, and detection and avoidance of obstacles. The system provides farmers with a modular product capable of pollinating a field of female plants in an industrial scale farming environment. The system identifies and locates fruit arms, senses wind speed and direction, and attains the proper location from which to dispense pollen using an autonomous or remote pollen dispensing system.

By using and relying on the methods and systems described herein, the pollination system identifies a particular plant within a plot, identifies target areas of the plant to pollinate correlating to positioning the vehicle over the plant based on wind speed and direction, dispenses an appropriate amount of pollen to the target areas of the plant, and moves to another plant in the plot to repeat the process. As such, the systems and methods described herein may be employed to automatically pollinate multiple plants in a plot, targeting the pollen to flower locations on the plant, and dispensing an appropriate amount of pollen. Hence, the systems and methods described herein allow for cost savings through reduction of labor, reduced pollen waste, and more accurate and efficient plant pollination, and also reduce the risk of injury previously borne by manual pollinators.

The technology described herein may be used to pollinate any desired plant. Aircraft pollination is particularly useful for taller plants, and the technology described herein is useful for plants up to eighty feet tall or taller, depending on the capabilities of the aircraft.

Example System Architecture

Turning now to the drawings, in which like numerals indicate like (but not necessarily identical) elements throughout the figures, example embodiments are described in detail.

Figure 1:
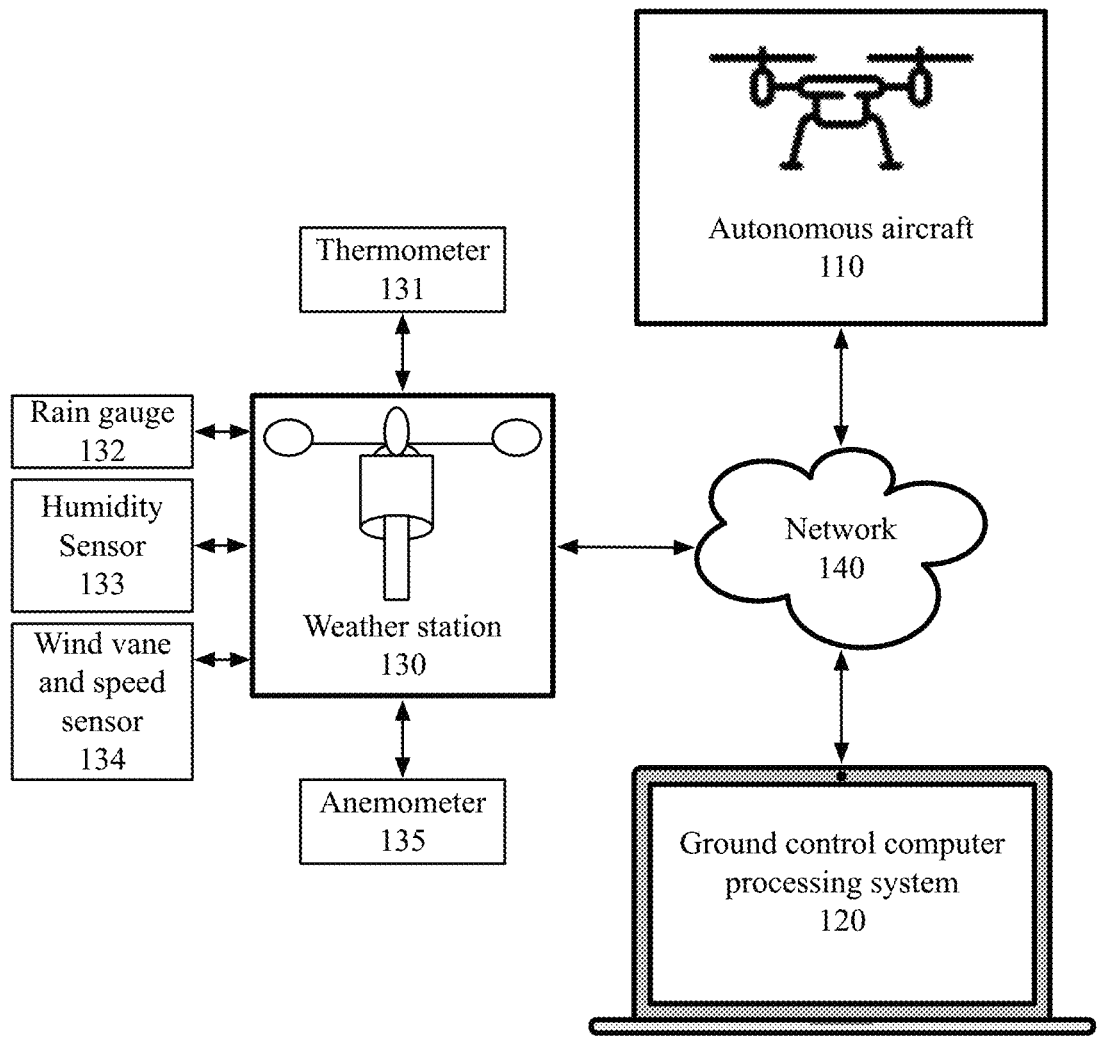
FIG. 1 is a block diagram depicting a pollinating system for autonomous aircraft pollination of plants.

FIG. 1 is a block diagram depicting a pollinating system 100 for autonomous aircraft pollination of plants, in accordance with certain examples. As shown in FIG. 1, the pollinating system 100 comprises one or multiple autonomous aircraft 110, a ground control computer processing system ("ground control system") 120, and a weather station 130. In operation, the ground control system receives weather inputs from the weather station 130 via one or more networks 140, such as wind speed and direction, and communicates the weather inputs to the drone via one or more networks 140. The ground control system 120 also communicates map, coordinate, and route information to the drone to identify a plot of plants to be pollinated and individual plants within the plot. The drone executes the route, adjusting for wind speed and direction, to pollinate the individual plants in the plot.

The ground control system 120 and the drone each include a device having a communication module capable of transmitting and receiving data over one or more of the networks 140. Each network 140 can include any wireless network or combination of networks, such as a wireless local area network ("WLAN"), a cellular, LTE, or other mobile communication network, Bluetooth, NFC, Wi-Fi, or any combination thereof or any other appropriate architecture or system that facilitates the communication of signals, data, information, and/or messages. Throughout this specification, it should be understood that the terms "data" and "information" are used interchangeably herein to refer to text, images, audio, video, or any other form of information that can exist in a computer-based environment.

The ground control system 120 can include a server, desktop computer, laptop computer, tablet computer, smart phone, handheld computer, personal digital assistant ("PDA"), or any other wired or wireless, processor-driven device. The autonomous aircraft 110 and the weather station 130 also can include one or more processor-driven devices. In the example architecture depicted in FIG. 1, the weather station 130, ground control system 120, and autonomous aircraft 110 may be operated or configured by users or other operators.

The weather station 130 is a portable or fixed computing or analog system that houses weather sensors, such as a thermometer 131, a rain gauge 132, a humidity sensor 133, a wind vane and speed sensor 134, an anemometer 135, and other suitable weather sensors. The weather station 130 collects weather information via the sensors to monitor weather activity at the plot for pollinating. The weather station 130 communicates the weather information to the ground control system 120. The weather information supports maneuvering the autonomous aircraft 110 to the desired location for pollinating a plant. Additionally, data such as wind speed and current rainfall in the area can require grounding of the autonomous aircraft 110 upon crossing a certain threshold.

The autonomous aircraft 110 may be a drone or other unmanned aircraft. For example, the autonomous aircraft 110 may be helicopter, quadcopter, or other aerial device capable of executing commands that are stored locally and/or received remotely. The autonomous aircraft 110 employs an onboard computing system comprising multiple components, including hardware, software, data storage, and other devices for communications, navigations, flight controls, image capturing, image processing, pollen dispensing, and any other suitable computerized, mechanical, or automated functions.

Figure 2:
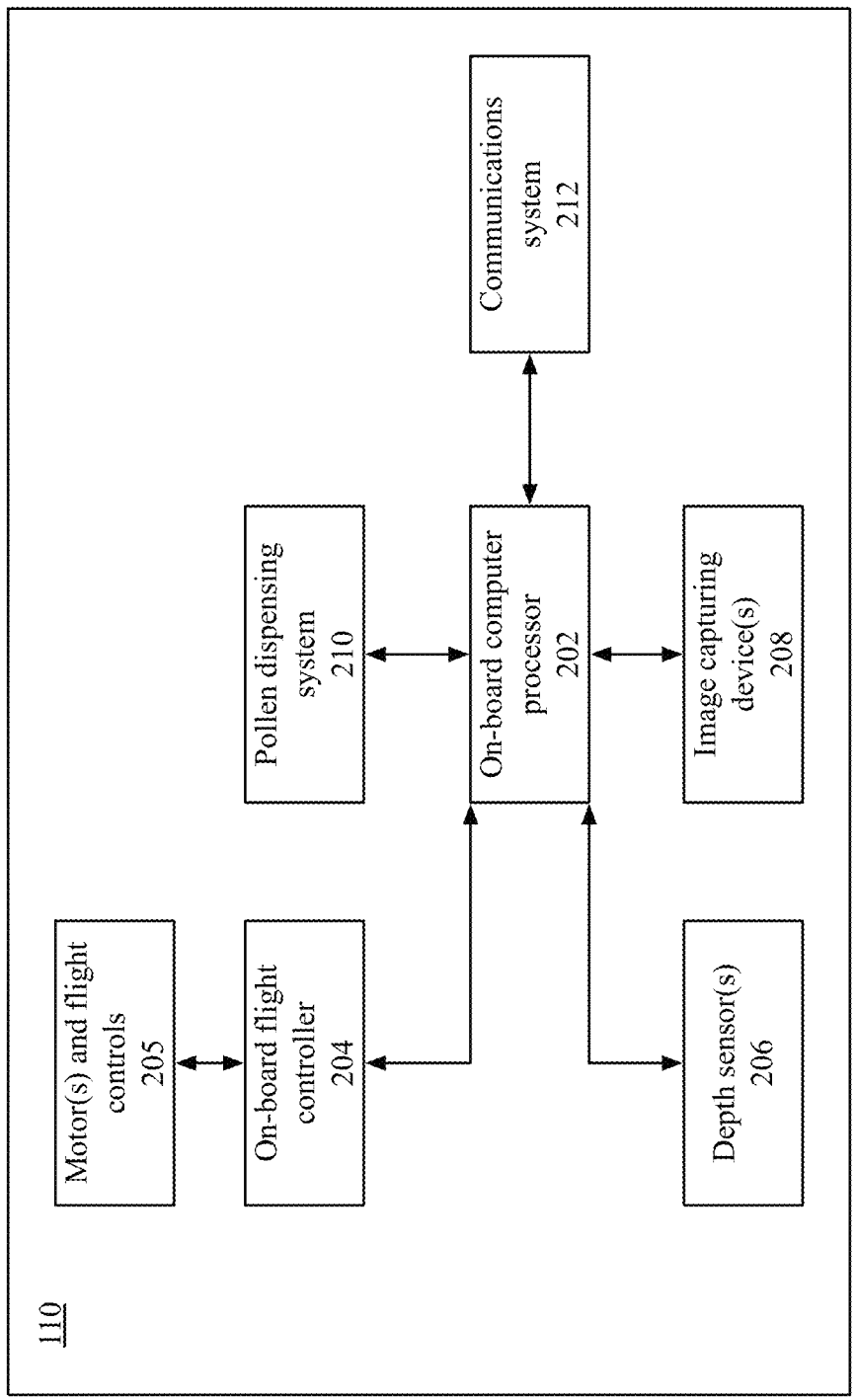
FIG. 2 is a block diagram depicting system architecture of an autonomous aircraft.

The system architecture of an autonomous aircraft 110 will be described in further detail with reference to FIG. 2. FIG. 2 is a block diagram depicting system architecture of an autonomous aircraft 110, in accordance with certain examples.

As depicted in FIG. 2, the autonomous aircraft 110 comprises an onboard processor 202, an onboard flight controller 204, one or more motors and flight controls 205, one or more depth sensors 206, one or more image capturing devices 208, a pollen dispensing system 210, and a communications system 212. A flight control system may comprise the one or more motors and/or the one or more flight controls together with the onboard flight controller 204 or other processor that controls the one or more motors and flight controls 205.

In operation, the communications system 212 receives route, weather, emergency command, and other information from the ground control system 120 via the network 140 and communicates the received information to the onboard processor 202. The onboard processor 202 communicates commands to the onboard flight controller 204 to maneuver the autonomous aircraft 110 through the route and with respect to individual plants to pollinate each plant. The onboard flight controller 204 executes the route and maneuvering via operation of the motors and flight controls 205. For example, the onboard flight controller 204 controls motors, propellers, and/or control surfaces to maneuver the autonomous aircraft 110 to desired locations. The onboard flight controller 204 also communicates aircraft system information to the onboard processor 202, such as battery levels and GPS location of the autonomous aircraft 110.

The autonomous aircraft 110 also comprises a navigation system, such as a global positioning system ("GPS") or other navigation system. For example, the autonomous aircraft 110 may have a mapping system stored in local storage that works alone or in conjunction with onboard GPS technology to assist the autonomous aircraft 110 with navigation. The onboard flight controller 204 or the onboard processor 202 may implement the navigation system for the autonomous aircraft.

The depth sensors 206 obtain height and/or distance information and communicate that height/distance information to the onboard processor 202. The height/distance information can be obtained on command from the onboard processor 202 or at specified intervals, locations, and/or other criteria. The height information comprises autonomous aircraft 110 height above ground or autonomous aircraft 110 height above a particular plant. At least one depth sensor 206 is positioned on the autonomous aircraft 110 to measure height of the autonomous aircraft 110 above ground or above a plant. Depth sensors 206 also may be positioned at other locations on the autonomous aircraft 110 to provide additional information. For example, depth sensors 206 can be positioned on the autonomous aircraft 110 in one or more locations to measure a distance from the autonomous aircraft 110 to objects within the flight path. With this information, the onboard processor 202 and onboard flight controller 204 can maneuver the autonomous aircraft 110 to avoid collisions.

The depth sensors 206 can comprise any suitable sensor that can determine a distance from the autonomous aircraft 110 to other objects or the ground. For example, the depth sensors 206 can comprise a barometric sensor for altitude detection above ground. The depth sensors 206 also can comprise optical, laser, RADAR, LIDAR, LADAR, SONAR, or any other suitable technology to determine distance from objects or the ground.

The image capturing devices 208 take images of the ground and plants under the autonomous aircraft 110, which can be obtained on command from the onboard processor 202 or at specified intervals, locations, and/or other criteria. The image capturing devices 208 communicate the images to the onboard processor 202. The images comprise a top view of one or more plants in the plot. The image capturing devices 208 may be a video camera or a still camera that capture images from a video feed or individually.

The onboard processor 202 uses the height and image information to determine a plant center and communicates plant center location information to the onboard flight controller 204. If desired, the onboard processor 202, or the onboard flight controller 204, may adjust the plant center information based on the weather information. The onboard flight controller 204 maneuvers the autonomous aircraft 110 above a particular plant based on the plant center information and notifies the onboard processor 202 when the autonomous aircraft 110 is in position. Then, the onboard processer instructs the pollen dispensing system 210 to release pollen from the autonomous aircraft 110. The pollen dispensing system 210 releases the pollen and communicates a confirmation to the onboard processor 202. The onboard processor 202 reports pollination of the particular plant to the ground control system 120 and then instructs the onboard flight controller 204 to maneuver the autonomous aircraft 110 to the next plant in the route.

In this manner, the onboard processor 202 uses the photographical, distance, waypoint, emergency, and other information provided by the depth sensors 206, image capturing devices 208, ground control system 120, and any other input to create and execute a movement plan that will both keep the autonomous aircraft 110 out of danger and allow it to pollinate plants efficiently. Using this information, the system 100 creates vectors and waypoints to move the autonomous aircraft 110 to the correct locations to dodge obstacles or to pollinate a plant.

The autonomous aircraft 110 communicates with the ground control system 120 via the communications system 212, which comprises an antenna to transmit and receive information. The antenna and communication system 212 are configured to operate with the desired network(s), such as a cellular network, Wi-Fi network, LTE network, or other suitable network utilized by the ground control system 120 and/or the weather station 130. The communications system 212 constantly listens for communications from the ground control system 120, decodes the protocol of those communications, and inputs the data into the onboard processor 202. This received data includes navigational, status, emergency, and other information. The communications system 212 also transmits data to the ground control system 120 to update the current status of the autonomous aircraft 110.

Figure 13:
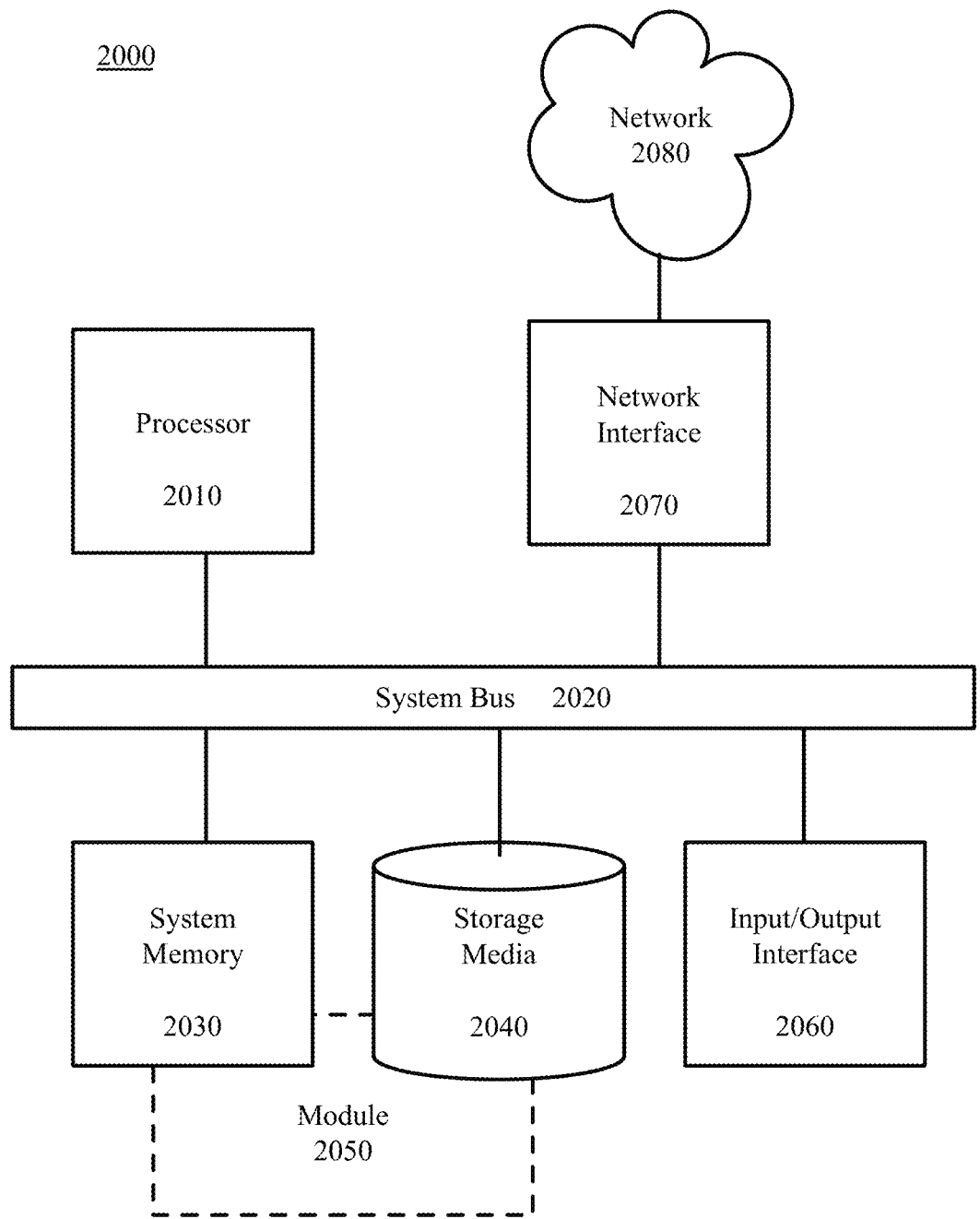
FIG. 13 is a block diagram depicting a computing machine and a module.

The weather station 130, ground control system 120, autonomous aircraft 110, and any other network computing devices or other computing machines associated with the technology presented herein may be any type of computing machine, such as, but not limited to, those discussed in more detail with respect to FIG. 13. For example, each device can include any suitable processor-driven device. Furthermore, any functions, applications, or components associated with any of these computing machines, such as those described herein or any others (for example, scripts, web content, software, firmware, hardware, or modules) associated with the technology presented herein may by any of the components discussed in more detail with respect to FIG. 13.

The network connections illustrated are examples and other means of establishing a communications link between the computers and devices can be used. The computing machines discussed herein may communicate with one another, as well as with other computing machines or communication systems over one or more networks. Each network may include various types of data or communications networks, including any of the network technology discussed with respect to FIG. 13.

Additionally, those having ordinary skill in the art and the benefit of this disclosure will appreciate that the devices illustrated in FIGS. 1 and 2 may have any of several other suitable computer system configurations.

Example Processes

The methods illustrated in FIGS. 3 through 12 are described hereinafter with respect to the components of the pollination system 100 and the autonomous aircraft 110. The methods of FIGS. 3 through 12 describe pollination of plants using autonomous aircraft 110. The methods of FIGS. 3 through 12 may also be performed with other systems and in other environments.

Figure 3:
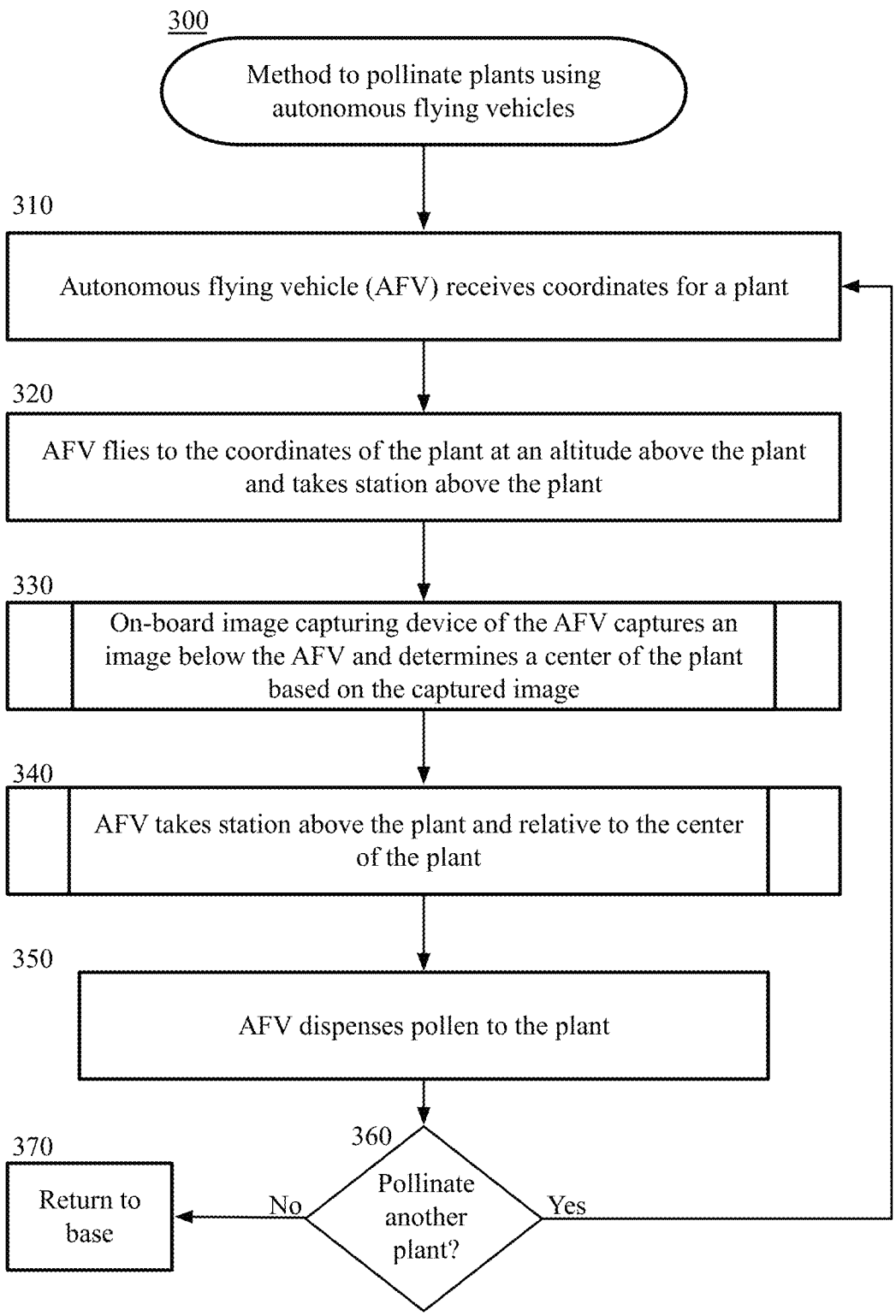
FIG. 3 is a block flow diagram depicting a method to pollinate plants using autonomous aircraft.

FIG. 3 is a block flow diagram depicting a method 302 to pollinate plants using autonomous aircraft 110. In block 310, an autonomous aircraft 110 receives coordinates for a plant to be pollinated in a plot of plants. For example, a particular plant can be targeted for pollination. In this case, the ground control system 120 communicates coordinates for the plant to the autonomous aircraft. In another example, a route identifying multiple plants to be pollinated can be generated. The route identifies coordinates, or waypoints, for each plant to be pollinated and an order in which the plants are to be pollinated. In this case, the ground control system 120 communicates the route to the autonomous aircraft 110, and the onboard processor 202 of the autonomous aircraft 110 communicates the coordinate information to the onboard flight controller 204.

In block 320, the autonomous aircraft 110 identifies a plant to be pollinated, flies to the coordinates of the plant, and takes station above the plant. For example, the onboard flight controller 204 reads the coordinates of the plant identified for pollination, or reads the coordinates of the first plant in the route of plants to be pollinated. The onboard flight controller 204 of the autonomous aircraft 110 commands the motors and flight controls 205 to maneuver the autonomous aircraft 110 above the plant by moving to the specified coordinates.

In block 330, an onboard image capturing device 208 of the autonomous aircraft 110 captures an image below the autonomous aircraft 110 and determines a center of the plant based on the captured image. Block 330 will be described in further detail hereinafter with reference to FIG. 4.

Figure 4:
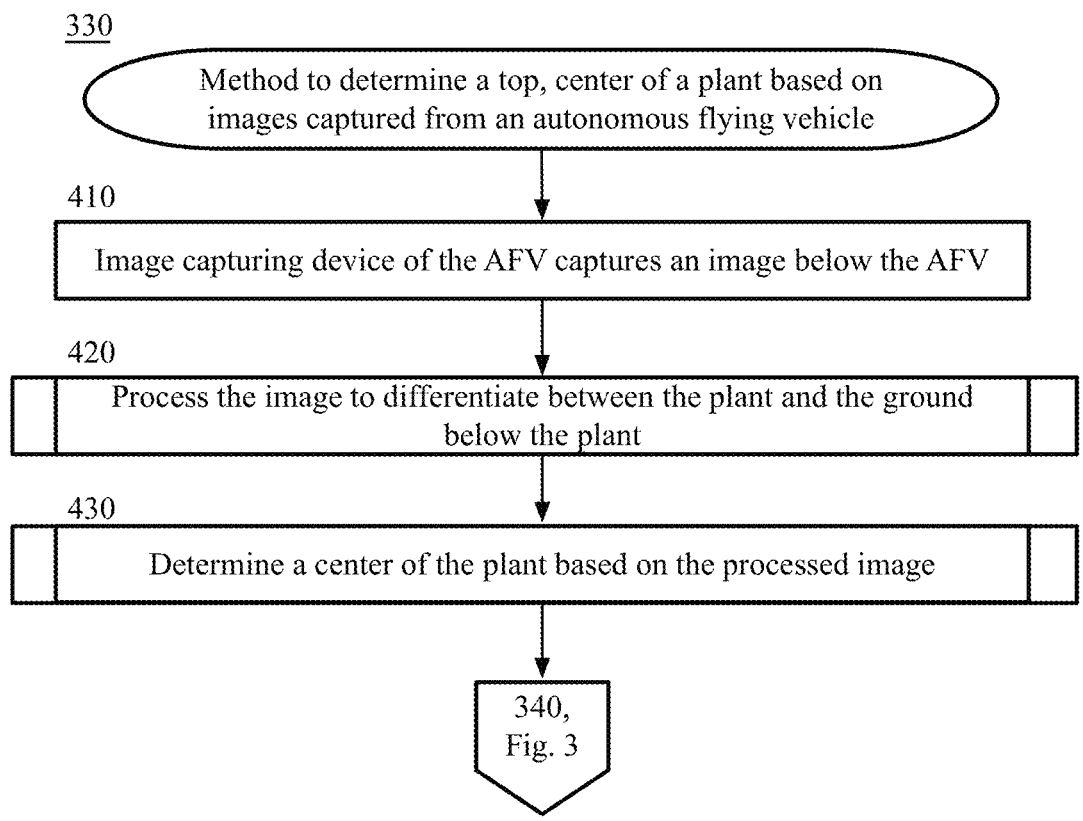
FIG. 4 is a block flow diagram depicting a method to determine a top, center of a plant based on one or more images captured from an autonomous aircraft.

FIG. 4 is a block flow diagram depicting a method 330 to determine a top, center of a plant based on one or more images captured from an autonomous aircraft 110, in accordance with certain examples. In block 410, the image capturing device 208 of the autonomous aircraft 110 captures an image below the autonomous aircraft 110 and communicates the captured image to the onboard processor 202. In block 420, the captured image is processed to differentiate between the plant and the ground below the plant. While any suitable image processing technique can be used to process the image to differentiate between the plant and the ground below the plant, an exemplary process 420 will be described with reference to FIG. 5.

Figure 5:
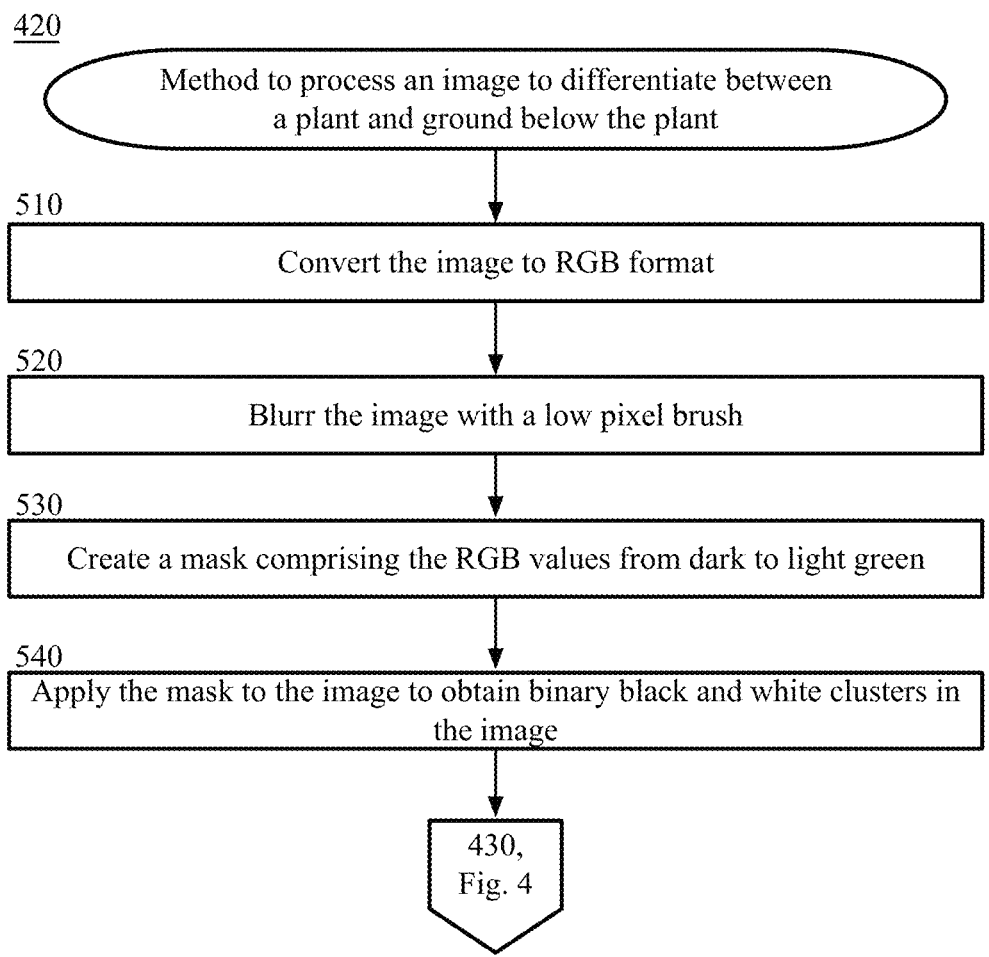
FIG. 5 is a block flow diagram depicting a method to process an image to differentiate between a plant and ground below the plant.

FIG. 5 is a block flow diagram depicting a method 420 to process an image to differentiate between a plant and ground below the plant, in accordance with certain examples. In block 510, the onboard processor 202 converts the image to an RGB format. In block 520, the onboard processor 202 blurs the image with a low pixel brush. For example, the image can be blurred using a 10×10 pixel brush application.

In block 530, the onboard processor 202 creates a mask of the image to comprise the RGB values from dark light to dark green. Then, in block 540, the onboard processor 202 applies the mask to the image to obtain binary black-and-white clusters in the image. For example, the mask identifies all green values from block 530 as white clusters, and identifies all other color values as black clusters.

Figure 8A:
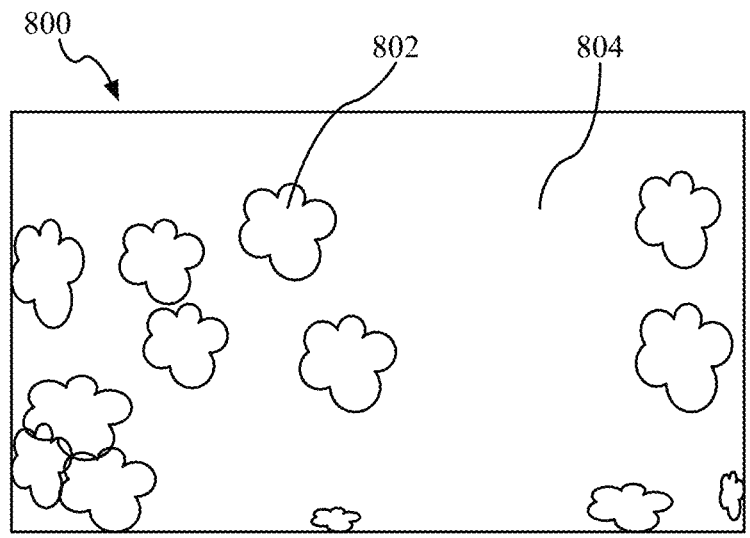
FIGS. 8A and 8B illustrate an image and the resulting processed image, respectively, which differentiates between the plant and the ground below the plant.
Figure 8B:
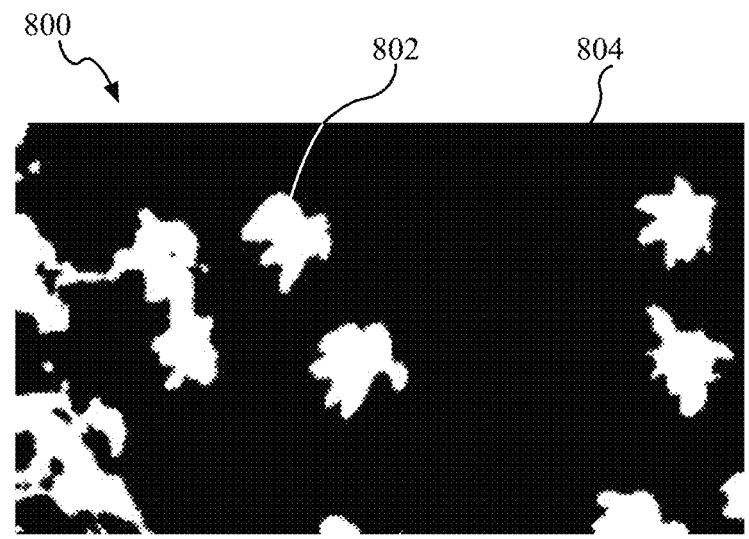

FIGS. 8A and 8B illustrate an image and the resulting processed image that differentiates between the plant and the ground below the plant, in accordance with certain examples. FIG. 8A is an image 800 showing palm trees 802 and the sandy ground 804 below the palm trees 802. FIG. 8B shows a resulting processed image 800 in which the green leaves of the palm trees 802 from FIG. 8A have been converted into white clusters, and the remaining non-green portions of the image have been converted to black clusters, including the brown, sandy ground 804. In this manner, the white clusters representing the plants are differentiated from the black clusters representing the ground and other items in the image.

From block 540, the message 420 proceeds to Block 430 in FIG. 4. Referring back to FIG. 4, in block 430, the center of the plant is determined based on the processed image. Block 430 is described in further detail hereinafter with reference to FIG. 6.

Figure 6:
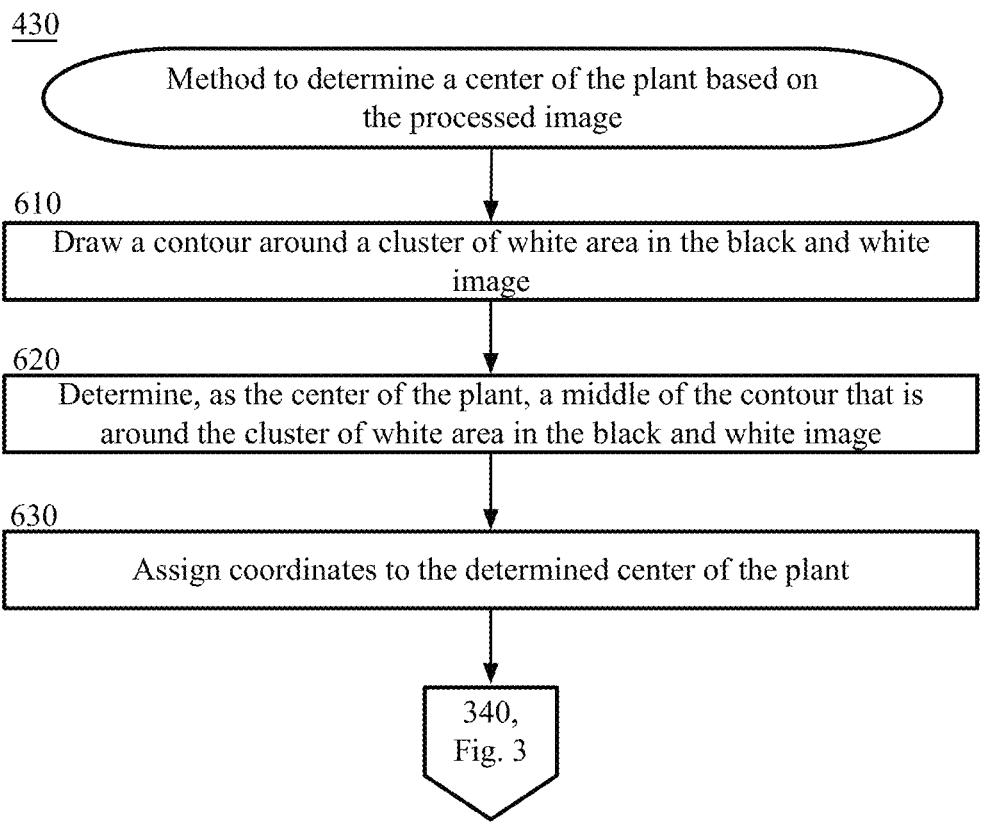
FIG. 6 is a block flow diagram depicting a method to determine a center of a plant based on a processed image.

FIG. 6 is a block flow diagram depicting a method 430 to determine a center of a plant based on the processed image from block 420, in accordance with certain examples. In block 610, the onboard processor 202 draws a contour around a cluster of white area in the black-and-white image. For example, a circle can be drawing around each cluster of white area in the black-and-white image. For a particular cluster of white area, the circle can be sized just large enough to capture the entirety of the white area. Any suitable contour can be used. For example, the contour can be a circle, rectangle, or other polygon, as desired.

In block 620, the onboard processor 202 determines the center of the plant by determining a middle of the contour that is around the cluster of white area in the black-and-white image. For this step, the process 430 can identify the cluster of white area that is closest to the center below the autonomous aircraft 110 as the target plant. Then, the onboard processor 202 determines the middle of the contour around the closest white area. For example, the middle of the circle or other contour around the white area is calculated based on the radius or other dimensions of the contour. These dimensions can be extracted based on pixel size of the image and a distance from the plant, or any other suitable method.

Then, in block 630, the onboard processor 202 assigns coordinates to the determined center of the plant. For example, the center of the plant can be determined relative to the current location of the autonomous aircraft 110. Based on the current location, such as latitude and longitude, of the autonomous aircraft 110 relative to the center of the plant, a vector can be determined from the current coordinates to the center of the planet. With that information, the coordinates of the center of the planet also can be determined by calculating the plant coordinates based on the vector from the current coordinates.

Figure 9A:
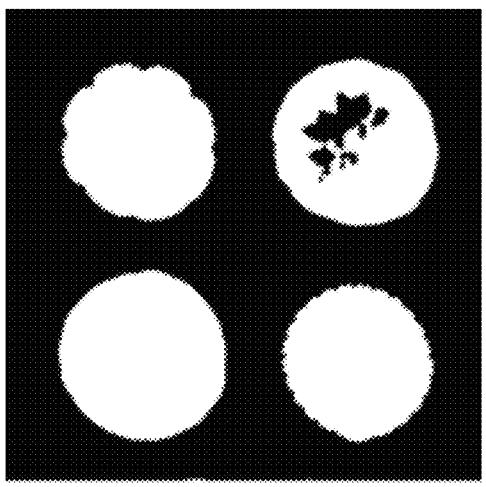
FIGS. 9A and 9B are illustrations depicting image processing to determine a center of a plant.
Figure 9B:
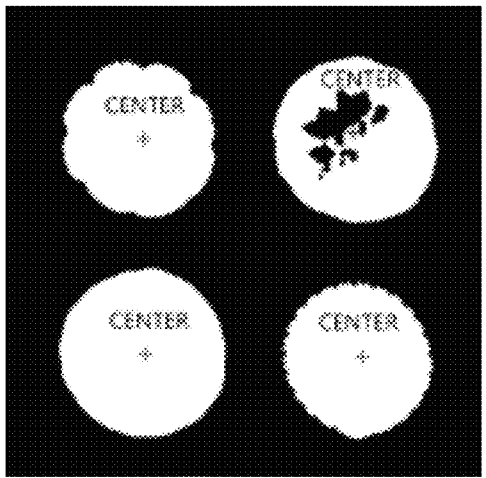

FIGS. 9A and 9B are illustrations depicting image processing to determine a center of a plant, in accordance with certain examples. As shown in FIG. 9A, four clusters of white area were identified in the processed image, and contours were drawn around each cluster of white area. As shown in FIG. 9B, the center (identified with a "+" in FIG. 9B) of each contour was calculated based on mathematical relationships of the dimensions and outline of the contour. The center of the plant is established as the center of the contour.

Referring back to FIG. 4, after determining the center of the plant based on the processed image in block 430, the method 330 proceeds to block 340 in FIG. 3.

In block 340 of FIG. 3, the autonomous aircraft 110 takes station above the plant and relative to the center of the plant. Block 340 is described in further detail hereinafter with reference to FIG. 7.

FIG. 7 is a block flow diagram depicting a method 340 for an autonomous aircraft 110 to take station above a plant and relative to the center of the plant, in accordance with certain examples. In block 710, the onboard processor 202 of the autonomous aircraft 110 reads the coordinates for the center of the plant. The coordinates for the center of the plant were determined previously in block 330 (see block 630 of FIG. 6).

In block 720, the onboard processor 202 determines whether to account for wind or other weather factors in determining a location at which the autonomous aircraft 110 will dispense pollen to the plant. If the onboard processor 202 will not account for wind or other weather factors, then the method 340 branches to block 730. In block 730, the onboard processor 202 sets the dispensing location as the center of the plant, and assigns the coordinates of the center of the plant as the dispensing location.

Referring back to block 720, if the onboard processor 202 will account for wind or other weather factors, then the method 340 branches to block 740. In block 740, the onboard processor 202 determines the effect of wind speed and direction of dispensed pollen based on a height of the autonomous aircraft 110 above the plant. Using the wind speed and direction, the height of the autonomous aircraft 110 above the plant, and other variables, such as a density of the pollen, the onboard processor 202 can calculate how the wind will affect dispersal of the pollen as the pollen falls to the ground. For example, the onboard processor 202 can calculate a vector representing the distance and direction the pollen will disperse in the time the pollen falls from the autonomous aircraft 110 to the top plant, based on the given variables. The height of the autonomous aircraft 110 above the plant can be determined based on a standard height above the plant at which the autonomous aircraft 110 is programmed to dispense pollen. Alternatively, the height of the autonomous aircraft 110 above the plant can be determined based on inputs from the depth sensor 206, or based on any suitable process. The wind speed and direction can be determined based on weather inputs from the weather station 130 communicated to the autonomous aircraft 110 via the ground control system 120.

Then, in block 750, the onboard processor 202 determines a location offset from the center of the plant from which the autonomous aircraft 110 should dispense the pollen. For example, the onboard processor 202 adds the vector from block 740 to the coordinates for the center of the plant to determine the offset location. Dispensing pollen from the offset location allows the wind to disperse the pollen across a desired area of the top of the plant as the pollen falls toward the ground, and may prevent or reduce the pollen missing the plant. In block 760, the onboard processor 202 sets the offset location as the dispensing location.

From either block 730 or block 760, the method 340 proceeds to block 770. In block 770, the autonomous aircraft 110 is maneuvered to the dispensing location. The onboard processor 202 communicates the dispensing location, and instructions to maneuver the autonomous aircraft 110 to the dispensing location, to the onboard flight controller 204, and the onboard flight controller 204 operates the motors and flight controls 205 in accordance with the instructions to maneuver the autonomous aircraft 110 to the dispensing location. The instructions include the coordinates of the dispensing location and the height above the plant for dispensing pollen.

FIGS. 10A, 10B, 10C, and 10D illustrate execution of the instructions to position the autonomous aircraft 110 in the dispensing location above a plant.

With reference to FIG. 10A, the autonomous aircraft 110 maneuvers (per block 320 of FIG. 3) to the coordinates for the location of the plant (as provided in block 310 of FIG. 3). The image capturing device 208 then captures an image below the autonomous aircraft 110. The field of view of the image capturing device 208 below the autonomous aircraft 110 is depicted by the square outline in FIGS. 10A-10D. The method of block 330 is executed to determine the center of the plant in the image. If more than one plant is identified in the image, the plant closest to the autonomous aircraft 110 is chosen, which is likely the plant intended to be pollinated at the specified coordinates.

After identifying the closest plant, FIGS. 10B-10D illustrate an example of execution of the method of block 340 to maneuver the autonomous aircraft 110 above the plant. In FIG. 10B, the autonomous aircraft 110 is maneuvered directly over the center of the closest plant. In FIG. 10C, the autonomous aircraft 110 descends to the height above the plant specified for dispensing pollen. Finally, in FIG. 10D, the autonomous aircraft 110 maneuvers to the offset location to place the autonomous aircraft 110 in position to dispense pollen by accounting for wind speed and direction.

Referring back to FIG. 3, after maneuvering the autonomous aircraft 110 to the dispensing location, the method 300 proceeds to block 350, and the autonomous aircraft 110 dispenses pollen to the plant.

The pollen dispensing system 210 of the autonomous aircraft 110 can comprise any suitable dispensing system. In operation, the onboard flight controller 204 notifies the onboard processor 202 that the autonomous aircraft 110 is positioned at the dispensing location. Then, the onboard processor 202 instructs the pollen dispensing system 210 to dispense pollen from the autonomous aircraft 110. The pollen dispensing system 210 receives the instruction, dispenses pollen, and communicates a "pollen dispensed" signal to the onboard processor 202.

Example pollen dispensing systems 210 include processor-controlled systems, electro-mechanical systems, and combinations of these systems. In a processor-controlled system, a processor of the pollen dispensing system 210 receives the instruction to dispense pollen and executes program instructions stored in the processor to actuate mechanical mechanisms to release pollen from the pollen dispensing system 210. In an electro-mechanical system, the onboard processor 202 sends an electrical signal to the pollen dispensing system 210, which actuates mechanical operation of a motor that opens and closes an aperture to dispense the pollen and that returns an electrical "completion" signal to the onboard processor 202.

The pollen dispensing system 210 includes a device capable of dispensing pollen, a dry substance. In an example embodiment, the pollen dispensing system 210 comprises a three disk system in a canister that holds the pollen. The three disks are layered at a bottom opening of the canister. The upper and lower disks are fixed in the canister, while the middle disk is attached to a stepper motor via a spindle. The middle disk rotates when the stepper motor is activated to rotate the spindle attached to the middle disk. Each disk comprises four cutouts that have a calculated area for dispensing a desired amount of pollen with a full rotation of the middle disk. The motor rotates when a signal is sent onboard processor 202 and received by a stepper motor controller. The stepper motor controller decodes the signal and provides a voltage to the stepper motor, thereby rotating the stepper motor. Rotation of the stepper motor rotates the spindle the desired number of rotations, which rotates the middle disk attach thereto to distribute the desired amount of pollen.

The cutouts in the upper and lower disks are aligned. As the middle disk rotates, the cutouts in the middle disk momentarily align with the cutouts in the upper and lower disks, thereby allowing pollen to fall from the canister through the disks. As the middle disk continues to rotate, the cutouts in the middle disc reach a position out of alignment with the upper and lower discs, thereby preventing further release of pollen from the canister. The cutouts can be sized to allow a desired amount of pollen release based on rotation of the middle disk. Additionally, the rotation speed of the spindle and middle disk can be increased or decreased to achieve a desired amount of pollen release, and the middle spindle may be turned a configurable amount of whole or partial turns to achieve a desired amount of pollen release. The canister and disks may be formed of printed ABS plastic or any suitable material.

Referring back to FIG. 3, after dispensing pollen to the plant in block 350, the method 300 proceeds to block 360. In block 360, the onboard processor 202 determines whether to pollinate another plant. If yes, the method 300 returns to block 310 and repeats the method 300 for another plant. For example, if the autonomous aircraft 110 is executing a route to pollinate multiple plants in a plot, then the autonomous aircraft 110 will proceed to pollinate the next plant in the route.

Referring back to block 360, if the onboard processor 202 determines that the autonomous aircraft 110 will not pollinate another plant, then the method 300 branches to block 370 in which the autonomous aircraft 110 is instructed to return to base and land. For example, if the autonomous aircraft 110 was instructed to pollinate a single plant, or if the plant pollinated in block 350 was the last plant in a route, then the autonomous aircraft 110 has completed its mission and returns to base.

Although various processes are described herein as being performed by a particular component of autonomous aircraft 110, such as the onboard processor 202 or the onboard flight controller 204, the scope of the technology described herein is not limited to such particular implementations. For example, the onboard processor 202 of the autonomous aircraft 110 is described as processing the image to determine the center of the plant and the dispensing location. However, the image capturing device 208 may perform such processing and communicate the results to the onboard processor 202 and/or the onboard flight controller 204. Alternatively, the image information and current location of the autonomous aircraft 110 can be communicated from the autonomous aircraft 110 to the ground control system 120 to process the image and determine the center of the plant and the dispensing location. In this case, the ground control system 120 communicates the dispensing location to the autonomous aircraft 110 for pollination of the plant. In this manner, any suitable computing device of the system 100 may perform the methods described herein.

The onboard processor 202 of the autonomous aircraft 110 regularly communicates information to the ground control system 120 to update the plant and plot records. For example, the onboard processor 202 of the autonomous aircraft 110 communicates determined center and height of the plant to the ground control system 120. The ground control system 120 then updates the record associated with the plant with the current center location and height. The updated center location is used in subsequent pollination attempts for the plant. The height information is used to monitor health of the plant and in subsequent pollination attempts.

Figure 11:
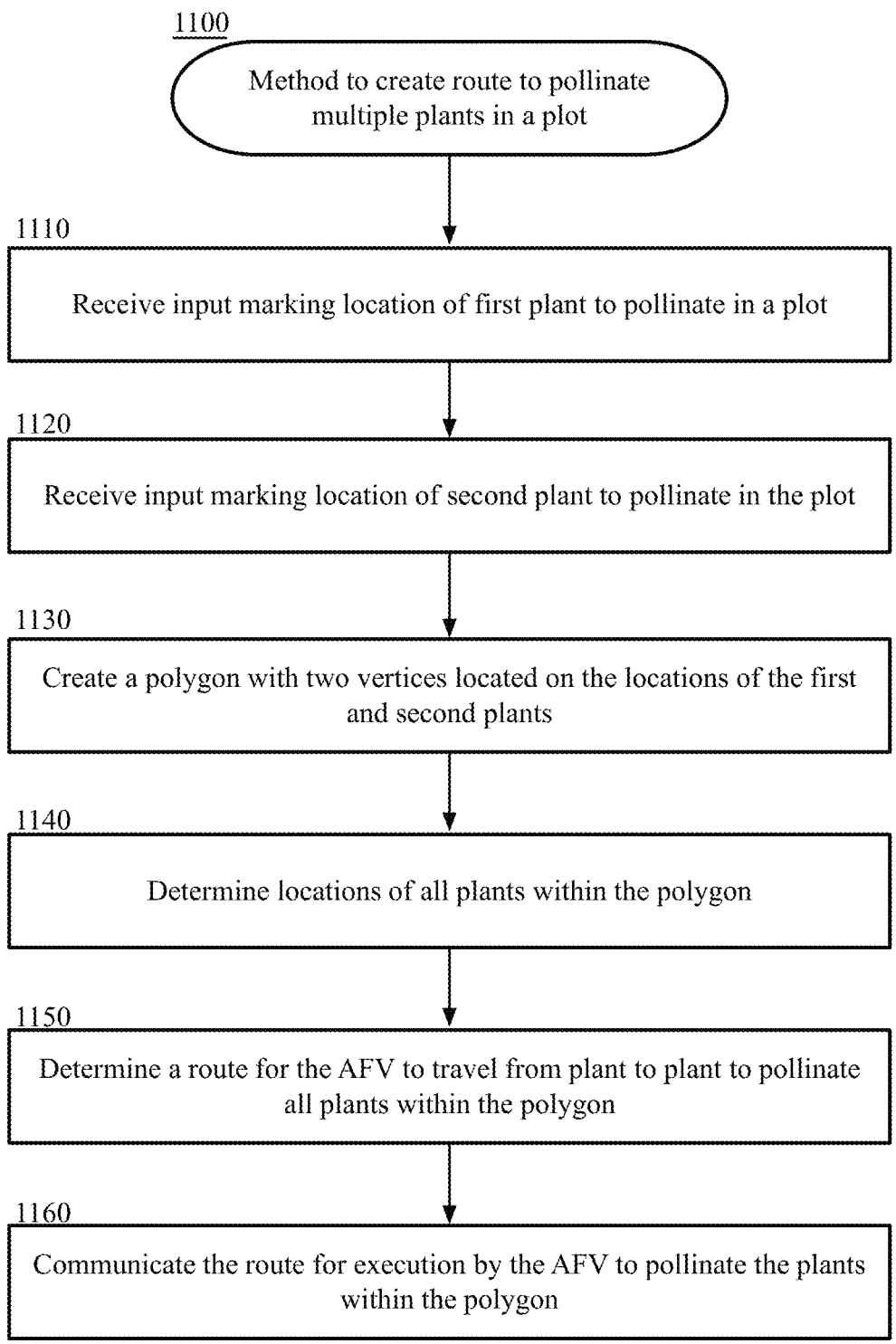
FIG. 11 is a block flow diagram depicting a method to create a route to pollinate multiple plants in a plot.
Figure 12A:
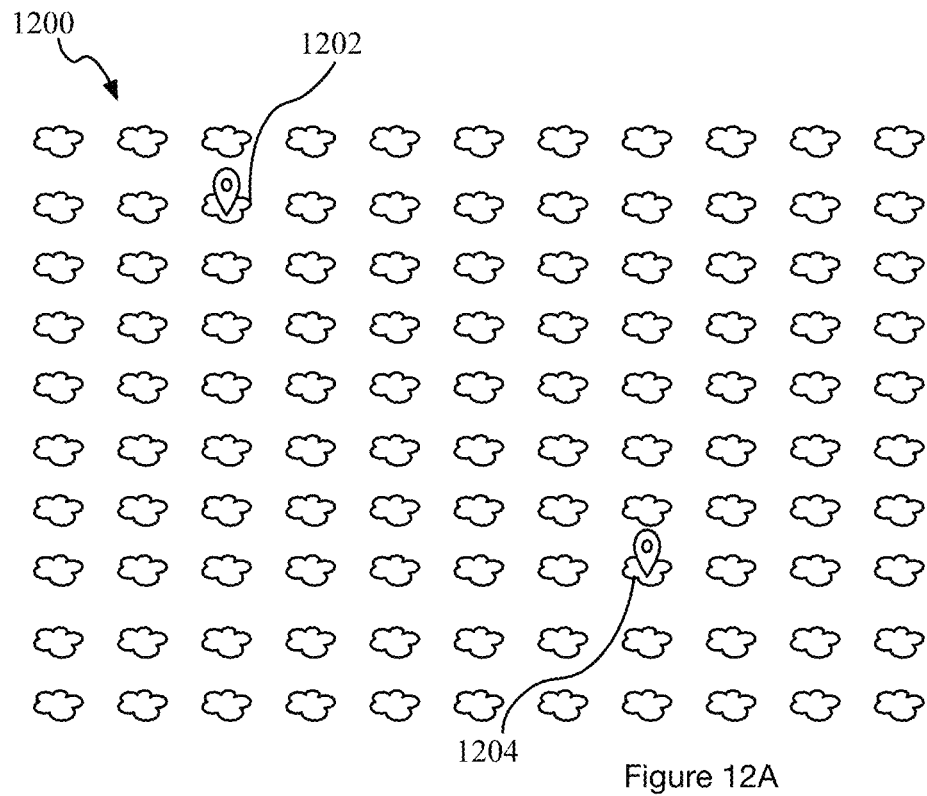
FIGS. 12A, 12B, and 12C are illustrations depicting a graphical user interface to identify boundaries of a plot of plants to be pollinated and to generate a route to pollinate the plants within the boundaries.
Figure 12B:
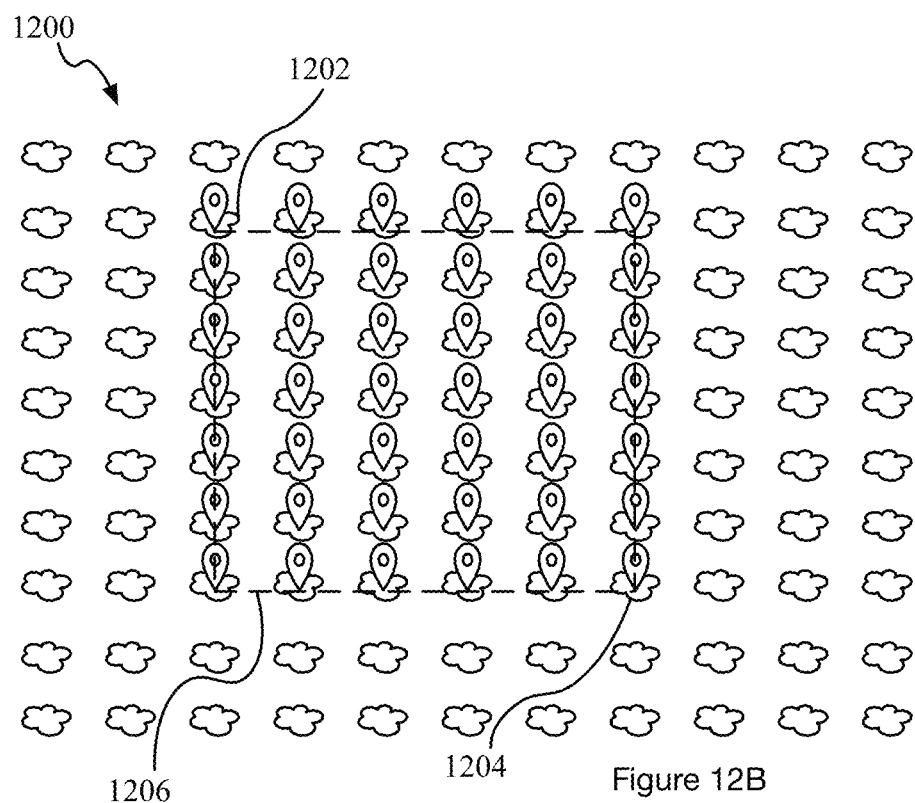
Figure 12C:
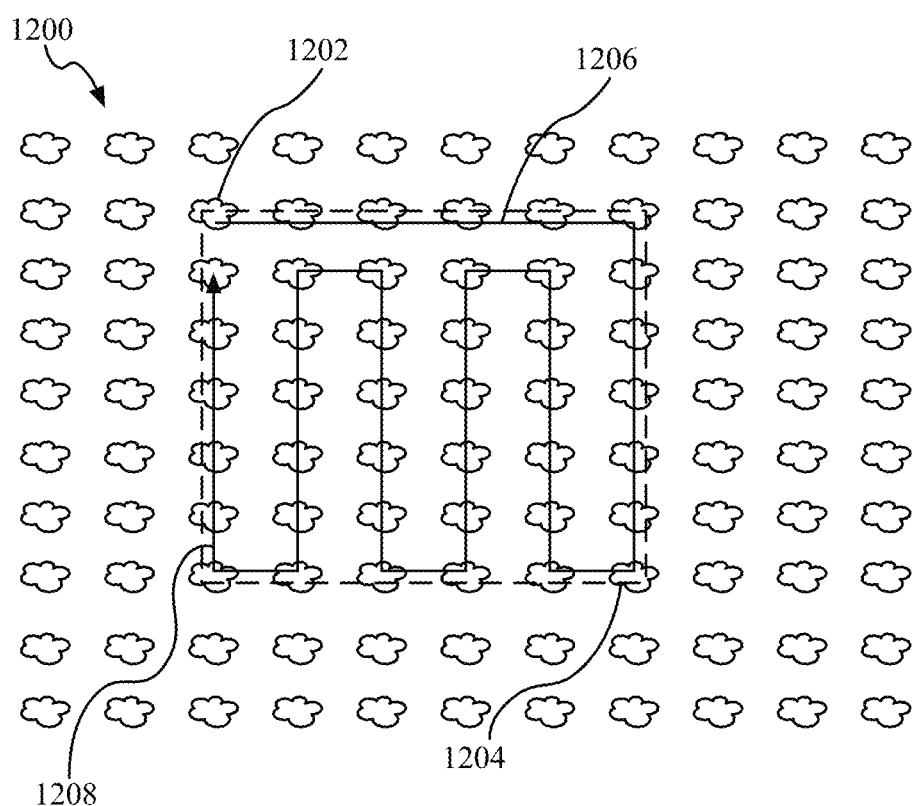

A method to create a route to pollinate multiple plants in a plot of land will now be described with reference to FIGS. 11 and 12A-12C. FIG. 11 is a block flow diagram depicting a method 1100 to create a route to pollinate multiple plants in a plot, in accordance with certain examples. FIGS. 12A, 12B, and 12C are illustrations depicting a graphical user interface to identify boundaries of a plot of plants to be pollinated and to generate a route to pollinate the plants within the boundaries, in accordance with certain examples.

In block 1110 of FIG. 11, and with reference to FIG. 12A, the ground control system 120 receives an input marking a location of a first plant 1202 to pollinate in a plot 1200 of plants. Additionally, in block 1120, the ground control system 120 receives an input marking a location of a second plant 1204 to pollinate in the plot 1200 of plants. For example, a user operates an input device to select the first and second plants 1202, 1204 on the user interface, and the ground control system 120 receives the inputs identifying the first and second plants 1202, 1204. The first and second plants 1202, 1204 indicate limits of an area encompassing plants to be pollinated. With reference to a mapping system and a database of plant locations in the plot 1200, the ground control system 120 associates actual locations of the first and second plants 1200, 1202 with the marked locations on the user interface, as indicated by the location symbols marking the first and second plants 1200, 1202. In an example as shown in FIG. 12A, the user interface displays a satellite mapping application showing of the plot 1200, and the ground control system 120 receives inputs identifying the first plant 1202 and the second plant 1204 on the mapping application displayed in the user interface.

In block 1130, and with reference to FIG. 12B, the ground control system 120 generates a polygon 1206 on the user interface, with two vertices of the polygon intersecting the locations of the first and second plants 1202, 1204. As shown in the example illustrated in FIG. 12B, the ground control system 120 generated a rectangle on the user interface, and two corners of the rectangle intersect the locations of the first and second plants 1202, 1204, respectively. Any suitable polygon or other shape may be utilized in block 1130 to capture a desired shape and size of the area of plants to be pollinated. For example, a pentagon or other multi-sided shape, or a circle, may be utilized.

In block 1140, and with reference to FIG. 12B, the ground control system 120 determines locations of all plants encompassed by the boundary defined by the polygon 1206, as indicated by the location symbols marking each of the plants encompassed by the boundary defined by the polygon 1206. The ground control system 120 maintains a database of the location of each plant in the plot 1200. For example, the location of each plant is defined by coordinates or waypoints, such as a latitude and longitude. Based on the locations of the first and second plants 1202, 1204 and the dimensions of the polygon 1206, the ground control system 120 determines a geographical area defined by the polygon 1206. Then, the ground control system 120 identifies each plant and its location within the geographical area defined by the polygon 1206. Other methods to identify locations of plants within the plot 1200 are suitable. For example, plant spacing can be input into the ground control system 120. Then, the ground control system 120 can calculate approximate locations of plants within the polygon 1206 based on the locations of the first and second plants 1202, 1204 and the spacing between plants. In operation, the autonomous aircraft 110 can compensate for inexact locations by identifying a closest plant to the location (as discussed previously with reference to FIG. 10A).

In block 1150, and with reference to FIG. 12C, the ground control system 120 determines a route 1208 for the autonomous aircraft 110 to travel from plant to plant to pollinate all plants located within the polygon 1206. Any suitable method to identify a route from plant to plant can be utilized. For example, the ground control system 120 may assign each plant to the route in the order that the plants are listed in the database. Alternatively, the ground control system 120 may identify a next plant that is closest to a current plant and assign the next plant to the route after the current plant. Other factors may be utilized to create the route, such as identifying plants in a row that are parallel to a side of the polygon 1206 until reaching a boundary of the polygon 1206, and then moving perpendicular to that side of the polygon 1206 to identify the next row of plants. That procedure can be repeated to input all rows of plants into the route. Additionally, multiple routes can be identified, route distances and times can be calculated for each route, and a particular route can be selected to minimize a time and/or distance traveled to pollinate all plants. The route comprises a list of waypoints (coordinates) in a specified order, where each waypoint corresponds to a plant location.

In block 1160, the ground control station communicates the route 1208 to the autonomous aircraft 110 for execution by the autonomous aircraft 110 to pollinate the plants within the polygon 1206.

Example Systems

The example systems and methods are described herein with respect to particular components of the example autonomous aircraft 110 pollinating system. However, any suitable components may be used to perform those methods and functions, and this disclosure is not limited to the particular components described herein.

The operations described herein can be implemented as executable code stored on a computer or machine readable non-transitory tangible storage medium (e.g., floppy disk, hard disk, ROM, EEPROM, nonvolatile RAM, CD-ROM, flash drive, etc.) that are completed based on execution of the code by a processor circuit implemented using one or more integrated circuits; the operations described herein also can be implemented as executable logic that is encoded in one or more non-transitory tangible media for execution (e.g., programmable logic arrays or devices, field programmable gate arrays, programmable array logic, application specific integrated circuits, etc.).

FIG. 13 depicts a computing machine 2000 and a module 2050 in accordance with certain examples. The computing machine 2000 may correspond to any of the various computers, servers, mobile devices, embedded systems, or computing systems presented herein. The module 2050 may comprise one or more hardware or software elements configured to facilitate the computing machine 2000 in performing the various methods and processing functions presented herein. The computing machine 2000 may include various internal or attached components, for example, a processor 2010, system bus 2020, system memory 2030, storage media 2040, input/output interface 2060, and a network interface 2070 for communicating with a network 2080.

The computing machine 2000 may be implemented as a conventional computer system, an embedded controller, a laptop, a server, a mobile device, a smartphone, a set-top box, a kiosk, a vehicular information system, one more processors associated with a television, a customized machine, any other hardware platform, or any combination or multiplicity thereof. The computing machine 2000 may be a distributed system configured to function using multiple computing machines interconnected via a data network or bus system.

The processor 2010 may be configured to execute code or instructions to perform the operations and functionality described herein, manage request flow and address mappings, and to perform calculations and generate commands. The processor 2010 may be configured to monitor and control the operation of the components in the computing machine 2000. The processor 2010 may be a general purpose processor, a processor core, a multiprocessor, a reconfigurable processor, a microcontroller, a digital signal processor (DSP), an application specific integrated circuit (ASIC), a graphics processing unit (GPU), a field programmable gate array (FPGA), a programmable logic device (PLD), a controller, a state machine, gated logic, discrete hardware components, any other processing unit, or any combination or multiplicity thereof. The processor 2010 may be a single processing unit, multiple processing units, a single processing core, multiple processing cores, special purpose processing cores, co-processors, or any combination thereof. According to certain examples, the processor 2010 along with other components of the computing machine 2000 may be a virtualized computing machine executing within one or more other computing machines.

The system memory 2030 may include non-volatile memories, for example, read-only memory (ROM), programmable read-only memory (PROM), erasable programmable read-only memory (EPROM), flash memory, or any other device capable of storing program instructions or data with or without applied power. The system memory 2030 may also include volatile memories, for example, random access memory (RAM), static random access memory (SRAM), dynamic random access memory (DRAM), and synchronous dynamic random access memory (SDRAM). Other types of RAM also may be used to implement the system memory 2030. The system memory 2030 may be implemented using a single memory module or multiple memory modules. While the system memory 2030 is depicted as being part of the computing machine 2000, one skilled in the art will recognize that the system memory 2030 may be separate from the computing machine 2000 without departing from the scope of the subject technology. It should also be appreciated that the system memory 2030 may include, or operate in conjunction with, a non-volatile storage device, for example, the storage media 2040.

The storage media 2040 may include a hard disk, a floppy disk, a compact disc read only memory (CD-ROM), a digital versatile disc (DVD), a Blu-ray disc, a magnetic tape, a flash memory, other non-volatile memory device, a solid state drive (SSD), any magnetic storage device, any optical storage device, any electrical storage device, any semiconductor storage device, any physical-based storage device, any other data storage device, or any combination or multiplicity thereof. The storage media 2040 may store one or more operating systems, application programs and program modules, for example, module 2050, data, or any other information. The storage media 2040 may be part of, or connected to, the computing machine 2000. The storage media 2040 may also be part of one or more other computing machines that are in communication with the computing machine 2000, for example, servers, database servers, cloud storage, network attached storage, and so forth.

The module 2050 may comprise one or more hardware or software elements configured to facilitate the computing machine 2000 with performing the various methods and processing functions presented herein. The module 2050 may include one or more sequences of instructions stored as software or firmware in association with the system memory 2030, the storage media 2040, or both. The storage media 2040 may therefore represent examples of machine or computer readable media on which instructions or code may be stored for execution by the processor 2010. Machine or computer readable media may generally refer to any medium or media used to provide instructions to the processor 2010. Such machine or computer readable media associated with the module 2050 may comprise a computer software product. It should be appreciated that a computer software product comprising the module 2050 may also be associated with one or more processes or methods for delivering the module 2050 to the computing machine 2000 via the network 2080, any signal-bearing medium, or any other communication or delivery technology. The module 2050 may also comprise hardware circuits or information for configuring hardware circuits, for example, microcode or configuration information for an FPGA or other PLD.

The input/output (I/O) interface 2060 may be configured to couple to one or more external devices, to receive data from the one or more external devices, and to send data to the one or more external devices. Such external devices along with the various internal devices may also be known as peripheral devices. The I/O interface 2060 may include both electrical and physical connections for operably coupling the various peripheral devices to the computing machine 2000 or the processor 2010. The I/O interface 2060 may be configured to communicate data, addresses, and control signals between the peripheral devices, the computing machine 2000, or the processor 2010. The I/O interface 2060 may be configured to implement any standard interface, for example, small computer system interface (SCSI), serial-attached SCSI (SAS), fiber channel, peripheral component interconnect (PCI), PCI express (PCIe), serial bus, parallel bus, advanced technology attached (ATA), serial ATA (SATA), universal serial bus (USB), Thunderbolt, Fire-Wire, various video buses, and the like. The I/O interface 2060 may be configured to implement only one interface or bus technology. Alternatively, the I/O interface 2060 may be configured to implement multiple interfaces or bus technologies. The I/O interface 2060 may be configured as part of, all of, or to operate in conjunction with, the system bus 2020. The I/O interface 2060 may include one or more buffers for buffering transmissions between one or more external devices, internal devices, the computing machine 2000, or the processor 2010.

The I/O interface 2060 may couple the computing machine 2000 to various input devices including mice, touch-screens, scanners, electronic digitizers, sensors, receivers, touchpads, trackballs, cameras, microphones, keyboards, any other pointing devices, or any combinations thereof. The I/O interface 2060 may couple the computing machine 2000 to various output devices including video displays, speakers, printers, projectors, tactile feedback devices, automation control, robotic components, actuators, motors, fans, solenoids, valves, pumps, transmitters, signal emitters, lights, and so forth.

The computing machine 2000 may operate in a networked environment using logical connections through the network interface 2070 to one or more other systems or computing machines across the network 2080. The network 2080 may include wide area networks (WAN), local area networks (LAN), intranets, the Internet, wireless access networks, wired networks, mobile networks, telephone networks, optical networks, or combinations thereof. The network 2080 may be packet switched, circuit switched, of any topology, and may use any communication protocol. Communication links within the network 2080 may involve various digital or analog communication media, for example, fiber optic cables, free-space optics, waveguides, electrical conductors, wireless links, antennas, radio-frequency communications, and so forth.

The processor 2010 may be connected to the other elements of the computing machine 2000 or the various peripherals discussed herein through the system bus 2020. It should be appreciated that the system bus 2020 may be within the processor 2010, outside the processor 2010, or both. According to certain examples, any of the processor 2010, the other elements of the computing machine 2000, or the various peripherals discussed herein may be integrated into a single device, for example, a system on chip (SOC), system on package (SOP), or ASIC device.

Examples may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing examples in computer programming, and the examples should not be construed as limited to any one set of computer program instructions. Further, a skilled programmer would be able to write such a computer program to implement an example of the disclosed examples based on the appended flow charts and associated description in the application text. Therefore, disclosure of a particular set of program code instructions is not considered necessary for an adequate understanding of how to make and use examples. Further, those skilled in the art will appreciate that one or more aspects of examples described herein may be performed by hardware, software, or a combination thereof, as may be embodied in one or more computing systems. Additionally, any reference to an act being performed by a computer should not be construed as being performed by a single computer as more than one computer may perform the act.

The examples described herein can be used with computer hardware and software that perform the methods and processing functions described previously. The systems, methods, and procedures described herein can be embodied in a programmable computer, computer-executable software, or digital circuitry. The software can be stored on computer-readable media. For example, computer-readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays (FPGA), etc.

The example systems, methods, and acts described in the examples presented previously are illustrative, and, in alternative examples, certain acts can be performed in a different order, in parallel with one another, omitted entirely, and/or combined between different example examples, and/or certain additional acts can be performed, without departing from the scope and spirit of various examples. Accordingly, such alternative examples are included in the scope of the following claims, which are to be accorded the broadest interpretation so as to encompass such alternate examples.

Although specific examples have been described above in detail, the description is merely for purposes of illustration. It should be appreciated, therefore, that many aspects described above are not intended as required or essential elements unless explicitly stated otherwise.

Modifications of, and equivalent components or acts corresponding to, the disclosed aspects of the examples, in addition to those described above, can be made by a person of ordinary skill in the art, having the benefit of the present disclosure, without departing from the spirit and scope of examples defined in the following claims, the scope of which is to be accorded the broadest interpretation so as to encompass such modifications and equivalent structures.

The invention claimed is:

1. A system to pollinate plants, comprising:
   a storage device associated with an autonomous aircraft;
   an image capture device onboard the autonomous aircraft;
   a pollen dispensing system;
   a flight control system onboard the autonomous aircraft; and
   a processor onboard the autonomous aircraft and communicatively coupled to the autonomous aircraft storage device, wherein the processor executes application code instructions that are stored in the storage device to cause the system to:
   operate the flight control system to maneuver the autonomous aircraft higher than a plant and in the general vicinity of the plant;

operate the image capture device to capture an image below the autonomous aircraft and including a top view of the plant;
process the image onboard the autonomous aircraft to differentiate between the plant and ground below the plant by:
converting the image to RGB format;
blurring the image with a low pixel brush;
creating a mask comprising the RGB values from dark to light green; and
applying the mask to obtain a binary black and white image;
determine a center of the plant based on the processed image;
operate the flight control system to position the autonomous aircraft above the plant and relative to the center of the plant; and
operate the pollen dispensing system to dispense pollen from the autonomous aircraft.

2. The system of claim 1, wherein the processor operates the flight control system to position the autonomous aircraft above the plant and relative to the center of the plant by positioning the autonomous aircraft autonomous aircraft directly above the center of the plant.

3. The system of claim 1, wherein the processor operates the flight control system to position the autonomous aircraft above the plant and relative to the center of the plant by positioning the autonomous aircraft offset from the center of the plant, wherein the offset is based on existing winds that affect dispensing the pollen.

4. The system of claim 3, further comprising a weather station that communicates the existing winds to the autonomous aircraft.

5. The system of claim 1, wherein the processor determines a center of the plant based on the processed image by:

drawing a contour around a cluster of white area in the black and white image; and calculating a middle of the contour.

6. The system of claim 5, wherein the processor positions the autonomous aircraft above the plant and relative to the center of the plant by:

determining a current location of the autonomous aircraft relative to a position of the middle of the contour;

determining at least one position adjustment to move the autonomous aircraft from the current location to the position of the middle of the contour; and instructing the autonomous aircraft to execute flight inputs to move the autonomous aircraft according to the position adjustment.

7. The system of claim 1, further comprising a ground control system that communicates a location of the plant to the autonomous aircraft, wherein the flight control system maneuvers the autonomous aircraft to the general vicinity of the plant based on the communicated location of the plant.

8. The system of claim 1, wherein the onboard processor comprises a single processor.

9. The system of claim 1, wherein the onboard processor comprises at least two processors, wherein a first processor operates the flight control system, and wherein a second processor processes the image to differentiate between the plant and ground below the plant and determines a center of the plant.

10. A method to position autonomous drones to dispense pollen to plants, comprising:

positioning an autonomous drone higher than a plant and in the general vicinity of the plant;

capturing an image below the autonomous drone and including a top view of the plant;

processing the image to differentiate between the plant and the ground below the plant with processor onboard the autonomous drone, wherein processing the image comprises:

converting the image to RGB format;

blurring the image with a low pixel brush;

creating a mask comprising the RGB values from dark to light green; and applying the mask to obtain a binary black and white image;

determining a center of the plant based on the processed image;

positioning the autonomous drone above the plant and relative to the center of the plant; and dispensing pollen from the autonomous drone.

11. The method of claim 10, wherein positioning the autonomous drone above the plant and relative to the center of the plant comprises positioning the autonomous drone directly above the center of the plant.

12. The method of claim 10, wherein positioning the autonomous drone above the plant and relative to the center of the plant comprises positioning the autonomous drone offset from the center of the plant, wherein the offset is based on existing winds that effect dispensing the pollen.

13. The method of claim 10, wherein determining a center of the plant based on the processed image comprises:

drawing a contour around a cluster of white area in the black and white image; and calculating a middle of the contour.

14. The method of claim 13, wherein positioning the autonomous drone above the plant and relative to the center of the plant comprises:

determining a current location of the autonomous drone relative to a position of the middle of the contour;

determining at least one position adjustment to move the autonomous drone from the current location to the position of the middle of the contour; and instructing the autonomous drone to execute flight inputs to move the drone according to the position adjustment.

15. The method of claim 10, further comprising receiving, from a ground control system, a location of the plant, wherein positioning the autonomous drone in the general vicinity of the plant is based on the received location of the plant.

16. A computer program product, comprising:

a non-transitory computer-readable medium having computer-readable program instructions embodied thereon that when executed by a computer cause the computer to pollinate plants, the computer readable instructions comprising:

computer-readable program instructions to position an autonomous drone higher than a plant and in the general vicinity of the plant;

computer-readable program instructions to capture an image below the autonomous drone and including a top view of the plant;

computer-readable program instructions to process the image to differentiate between the plant and the ground below the plant with a processor onboard the autonomous drone, wherein processing the image comprises:

converting the image to RGB format;

blurring the image with a low pixel brush;

creating a mask comprising the RGB values from dark to light green; and applying the mask to obtain a binary black and white image;

computer-readable program instructions to determine a center of the plant based on the processed image;

computer-readable program instructions to position the autonomous drone above the plant and relative to the center of the plant; and computer-readable program instructions to dispense pollen from the autonomous drone.

17. The computer program product of claim 16, wherein positioning the autonomous drone above the plant and relative to the center of the plant comprises positioning the autonomous drone offset from the center of the plant, wherein the offset is based on existing winds that effect dispensing the pollen.

18. The computer program product of claim 16,
wherein determining a center of the plant based on the processed image comprises:
drawing a contour around a cluster of white area in the black and white image; and
calculating a middle of the contour.

19. The computer program product of claim 18, wherein positioning the autonomous aircraft above the plant and relative to the center of the plant comprises:
determining a current location of the autonomous aircraft relative to a position of the middle of the contour;
determining at least one position adjustment to move the autonomous aircraft from the current location to the position of the middle of the contour; and
instructions to the autonomous aircraft to execute flight inputs to move the autonomous aircraft according to the position adjustment.

* * * * *